United States Patent [19]

Cardis

[11] 4,375,476

[45] Mar. 1, 1983

[54] INSECTICIDAL (2,6-DIMETHYL-3-SUBSTITUTED PHENYL)METHYL CYCLOPROPANECARBOXYLATES

[75] Inventor: Angeline B. Cardis, Florence, N.J.

[73] Assignee: FMC Corporation, Philadelphia, Pa.

[21] Appl. No.: 301,846

[22] Filed: Sep. 14, 1981

Related U.S. Application Data

[63] Continuation-in-part of Ser. No. 196,945, Oct. 14, 1980, abandoned.

[51] Int. Cl.³ ................... C07C 69/74; C07C 69/743; A01N 53/00
[52] U.S. Cl. .................................. 424/302; 424/304; 424/305; 260/454; 260/465 D; 560/124
[58] Field of Search ............... 560/124; 260/465 D, 260/454; 424/304, 305, 306, 302

[56] References Cited

U.S. PATENT DOCUMENTS

| | | | |
|---|---|---|---|
| 3,567,740 | 3/1971 | Matsui | 560/124 |
| 3,792,079 | 2/1974 | D'Orazio | 560/124 |
| 3,954,814 | 5/1976 | Mizutani | 560/124 |
| 3,979,424 | 9/1976 | Searle | 560/124 |
| 4,024,163 | 5/1977 | Elliott | 260/347.4 |
| 4,198,527 | 4/1980 | Henrick | 560/124 |
| 4,219,565 | 8/1980 | Roman | 560/124 |
| 4,243,677 | 1/1980 | Engel | 560/124 |
| 4,252,820 | 2/1981 | Lantzsch | 560/124 |
| 4,332,815 | 6/1982 | Engel | 424/274 |

FOREIGN PATENT DOCUMENTS

| | | | |
|---|---|---|---|
| 2407024 | 8/1974 | Fed. Rep. of Germany | 560/124 |
| 2290415 | 6/1976 | France . | |
| 2297834 | 9/1976 | France . | |
| 39-17182 | 8/1964 | Japan | 560/124 |
| 1401279 | 7/1975 | United Kingdom | 560/124 |

OTHER PUBLICATIONS

Elliott, Chem. Soc. Rev. 7, pp. 473–505, (1978).
Elliott, Pestic. Sci., 1, p. 49, (1970).
Elliott, Pestic. Sci., 1, p. 220, (1970).

Primary Examiner—Michael L. Shippen
Attorney, Agent, or Firm—R. L. Hansen; H. R. Ertelt

[57] ABSTRACT

(2,6-Dimethyl-3-substituted phenyl)methyl cyclopropanecarboxylates and insecticidal compositions containing these esters are useful for the control of a broad range of insects and acarids.

10 Claims, No Drawings

INSECTICIDAL (2,6-DIMETHYL-3-SUBSTITUTED PHENYL)METHYL CYCLOPROPANECARBOXYLATES

This application is a continuation-in-part of application Ser. No. 196,945 filed Oct. 14, 1980, now abandoned.

This invention pertains to the field of bioaffecting compositions; more specifically, it pertains to novel carboxylic acid esters which are pyrethroid insecticides, processes and intermediates thereto, insecticidal and acaricidal compositions containing the novel esters, and to the use of the compositions for controlling insects and acarids.

Pyrethroids have long been of interest as insecticides. Ever since it was discovered that the naturally occurring pyrethrins are organic esters, various synthetic modifications have been made in the carboxylic acid and in the alcohol moieties on either side of the ester linkage.

The carboxylic acid moiety in the aforesaid esters has often been a 2,2-dimethylcyclopropanecarboxylic acid. Insecticidal esters utilizing a 3-(2,2-dihaloethenyl)-2,2-dimethylcyclopropanecarboxylic acid moiety are disclosed in U.S. Pat. No. 4,024,163. Insecticidal esters utilizing a 3-(2-halo-3,3,3-trifluoropropenyl)-2,2-dimethylcyclopropanecarboxylic acid are disclosed in European Patent Office Publication No. 3 336. The 2,2,3,3-tetramethylcyclopropanecarboxylic acid moiety also leads to insecticidal esters as disclosed in U.S. Pat. No. 3,835,176.

Many variations in the alcohol moiety of the aforesaid esters have been disclosed also. Several derivatives of benzyl alcohol are known to yield insecticidal esters; for example, 3-phenoxybenzyl alcohol and α-cyano-3-phenoxybenzyl alcohol are disclosed in U.S. Pat. Nos. 4,024,163, and 4,130,657 discloses insecticidal pyrethroid esters containing a 3-phenylbenzyl alcohol moiety. Certain benzyl alcohols carrying 2,6-dimethyl substitution are known to yield insecticidal esters; e.g., U.S. Pat. No. 3,792,079 discloses the insecticidal activity of 2,6-dimethyl-4-nitrobenzyl chrysanthemate, and the insecticidal activity of 2,3,6-trimethylbenzyl chrysanthemate is known [See Elliott, et al., Pestic. Sci., 1, 220 (1970)].

It has now been found that insecticidal and acaricidal (2,6-dimethyl-3-substituted phenyl)methyl cyclopropanecarboxylates result from the combination of pyrethroid acid moieties, e.g., 2,2-dimethylcyclopropanecarboxylic acid moieties, and (2,6-dimethyl-3-substituted phenyl)methanol moieties, wherein the 3-substituents are selected from nitro, halo, including iodo, cyano, isothiocyanato, amino, and lower alkyl.

Like other pyrethroids, some of these new esters are capable of both geometrical and optical isomerism, the biological activity varying somewhat according to the specific isomer. The pure cis geometrical isomer of a (2,6-dimethyl-3-substituted phenyl)methyl cyclopropanecarboxylate is usually a more active insecticide and acaricide than the pure trans isomer, and the activity of a (2,6-dimethyl-3-substituted phenyl)methyl cyclopropanecarboxylate is a function of the cis/trans ratio. The pure optical isomers also display biological activity in varying degrees. The term "(2,6-dimethyl-3-substituted phenyl)methyl cyclopropanecarboxylate" employed herein is intended to include generically all optical and geometrical isomers of the named compounds and mixtures thereof. Unless explicitly stated otherwise, the term "lower" modifying alkyl means a linear or branched chain of 1-6, preferably 1-4, carbon atoms, and the terms "halo" or "halogen" mean fluorine, chlorine, or bromine.

The insecticidal and acaricidal (2,6-dimethyl-3-substituted phenyl)methyl cyclopropanecarboxylates of this invention are represented by the formula:

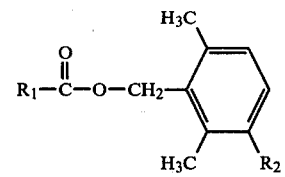

wherein $R_1$ is a pyrethroid acid residue, defined for this application as the residue of a cyclopropanecarboxylic acid which forms an insecticidal ester with m-phenoxybenzyl alcohol, e.g., 3-(2,2-dihaloethenyl)-2,2-dimethylcyclopropyl, 3-(2-halo-3,3,3-trifluoropropenyl)-2,2-dimethylcyclopropyl, and 2,2,3,3-tetramethylcyclopropyl, and $R_2$ is selected from nitro, halo, including iodo, cyano, isothiocyanato, amino, and lower alkyl. Among these compounds it is preferred that $R_1$ be either 3-(2,2-dihaloethenyl)-2,2-dimethylcyclopropyl, especially 3-(2,2-dichloroethenyl)-2,2-dimethylcyclopropyl, or 3-(2-halo-3,3,3-trifluoropropenyl)-2,2-dimethylcyclopropyl, especially 3-(2-chloro-3,3,3-trifluoropropenyl)-2,2-dimethylcyclopropyl, and that $R_2$ be selected from nitro, halo, including iodo, cyano, and lower alkyl. Of particular interest is (2,6-dimethyl-3-nitrophenyl)methyl 3-(2-chloro-3,3,3-trifluoropropenyl)-2,2-dimethylcyclopropanecarboxylate, especially the cis isomer.

Also within the contemplation of this invention are insecticidal or acaricidal compositions comprising an insecticidally or acaricidally effective amount of (2,6-dimethyl-3-substituted phenyl)methyl cyclopropanecarboxylate in admixture with an agriculturally acceptable carrier and a method of controlling insects or acarids which comprises applying to the locus where control is desired as insecticidally or acaricidally effective amount of (2,6-dimethyl-3-substituted phenyl)methyl cyclopropanecarboxylate.

The (2,6-dimethyl-3-substituted phenyl)methyl cyclopropanecarboxylates of this invention are prepared either by condensing a reactive acid derivative, e.g., the cyclopropanecarboxylic acid chloride, with a reactive phenylmethyl derivative, e.g., the (2,6-dimethyl-3-substituted phenyl)methanol, or by converting the 3-substituent in one ester into another 3-substituent, producing a different ester.

Preparation of the 3-(2,2-dihaloethenyl)-2,2-dimethylcyclopropanecarboxylic acid chlorides is disclosed in U.S. Pat. No. 4,024,163, the 3-(2-halo-3,3,3-trifluoropropenyl)-2,2-dimethylcyclopropanecarboxylic acid chlorides in European Patent Office Publication No. 3 336, and preparation of 2,2,3,3-tetramethyl cyclopropanecarboxylic acid chloride in U.S. Pat. No. 3,835,176, all of which are incorporated herein by reference.

The pure cis or trans cyclopropanecarboxylates are prepared either by reacting pure cis or pure trans cyclopropanecarboxylic acid derivatives with appropriate (2,6-dimethyl-3-substituted phenyl)methanols or by separating cis,trans mixtures using chromatographic techniques. The identities of the cis and trans isomers are established by reference to their nmr spectra, especially the patterns at 5.52–6.26 ppm and 6.08–7.58 ppm for the trans and cis isomers, respectively.

The pure 1R,cis-cyclopropanecarboxylates are prepared by reacting pure 1R,cis-cyclopropanecarboxylic acid chlorides with appropriate (2,6-dimethyl-3-substituted phenyl)methanols. The 1R,cis acid isomer is resolved from a 1R,1S-cis mixture by means of an amine salt as prescribed in Pestic. Sci., 5, 791 (1974). The identity of the isomer is established by reference to the optical rotation.

(2,6-Dimethyl-3-substituted phenyl)methanols, intermediates in the preparation of the aforesaid (2,6-dimethyl-3-substituted phenyl)methyl cyclopropanecarboxylates, are also compositions of matter which are within the scope of this invention. These intermediates are represented by the formula

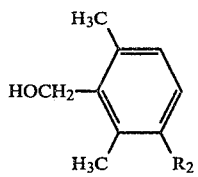

wherein $R_2$ is selected from nitro, halo, including iodo, cyano, isothiocyanato, amino, and lower alkyl, especially nitro, halo, including iodo, cyano, and amino.

The (2,6-dimethyl-3-substituted phenyl)methanols and cyclopropanecarboxylates of this invention are prepared by several methods, depending upon the particular compound desired. These methods are illustrated in the Examples which follow. Unless otherwise indicated, all temperatures are in degrees Celsius and pressures are in millimeters of mercury. Proton chemical shifts, taken from nmr spectra in $CDCl_3$, are reported in ppm with respect to tetramethylsilane.

EXAMPLE 1

Preparation of (2,6-Dimethyl-3-nitrophenyl)methyl Esters 2,6-Dimethyl-3-nitrobenzoic acid was prepared by nitrating 2,6-dimethylbenzoic acid. A solution of 2,6-dimethyl-3-nitrobenzoic acid (30 grams, 0.15 mole) in tetrahydrofuran (100 ml) was stirred under nitrogen. Borane-methyl sulfide complex (20 ml, 0.2 mole) was added dropwise at room temperature. When one fourth of the borane complex had been added the reaction mixture was brought to reflux. Reflux continued for one hour after complete addition of the borane complex. The reaction mixture was cooled to 0°, and cold methanol (500 ml) was added dropwise until foaming ceased and then added rapidly. The solvent was evaporated, and the crude product was dissolved in methylene chloride and washed with 2 N sodium hydroxide. The solvent was removed by evaporation to give (2,6-dimethyl-3-nitrophenyl)methanol (12.0 grams; mp 84°–92°).

Analysis:
Calc'd for $C_9H_{11}NO_3$: C, 59.66; H, 6.11; O, 7.73; Found: C, 59.11; H, 5.92; O, 8.08.
nmr: 1.60 (s,1H); 2.48–2.51 (m,6H); 4.78 (d,2H); 7.01–7.64 (m,2H).

(3-Amino-2,6-dimethylphenyl)methanol is prepared by reducing the corresponding 3-nitro compound.

Using dry glassware, pyridine (3.47 grams, 0.044 mole) was added to a stirred solution of (2,6-dimethyl-3-nitrophenyl)methanol (8.0 grams, 0.044 mole) in dry toluene (125 ml). The mixture was chilled to 0°, and a solution of 3-(2,2-dichloroethenyl)-2,2-dimethylcyclopropanecarboxylic acid chloride (9.78 grams, 0.043 mole, cis:trans 40:60) in dry toluene (25 ml) was added dropwise. The reaction mixture was stirred for 16 hours and slowly came to ambient temperature. The mixture was poured over crushed ice and extracted with three 50 ml portions of chloroform. The organic layer was washed successively with 50 ml portions of cold 5% hydrochloric acid, water, saturated aqueous sodium bicarbonate and water. The organic layer was dried over anhydrous magnesium sulfate, filtered and the solvent evaporated. The residue was chromatographed on silica gel and eluted, beginning with hexane and then increasing percentages of methylene chloride, to give two fractions, A (1.18 grams, mp 85°), which eluted first, and B (3.0 grams, mp 83°–84°).

Analysis of A:
Calc'd for $C_{17}H_{19}Cl_2NO_4$: C, 54.85; H, 5.14; Found: C, 55.09; H, 5.13.
nmr: 1.23 (s,3H); 1.25 (s,3H); 1.71–2.18 (m,2H); 2.46 (s,3H); 2.50 (s,3H); 5.24 (s,2H); 6.12–6.24 (d,1H); 7.06–7.74 (m,2H).

The nmr spectrum was consistent with (2,6-dimethyl-3-nitrophenyl)methyl cis-3-(2,2-dichloroethenyl)-2,2-dimethylcyclopropanecarboxylate. In the same way, but employing 1R,cis-3-(2,2-dichloroethenyl)-2,2-dimethylcyclopropanecarboxylic acid chloride, (2,6-dimethyl-3-nitrophenyl)methyl 1R,cis-3-(2,2-dichloroethenyl)-2,2-dimethylcyclopropanecarboxylate was prepared.

Analysis of B:
Calc'd for $C_{17}H_{19}Cl_2NO_4$: C, 54.85; H, 5.14; N, 3.76; Found: C, 55.11; H, 4.99; N, 3.54.
nmr: 1.17–1.26 (m,12H); 1.51–2.31 (m,4H); 2.43 (s,6H); 2.46 (s,6H); 5.23 (s,4H); 5.48–5.61 (d,1H); 6.33–6.46 (d,1H); 7.26–7.92 (m,4H).

The nmr spectrum was consistent with (2,6-dimethyl-3-nitrophenyl)methyl cis,trans-3-(2,2-dichloroethenyl)-2,2-dimethylcyclopropanecarboxylate (cis:trans 27:73).

Similarly, (2,6-dimethyl-3-nitrophenyl)methyl 3-(2,2-dibromoethenyl)- and 3-(2,2-difluoroethenyl)-2,2-dimethylcyclopropanecarboxylates are prepared from the appropriate acid chlorides.

In the same way, (2,6-dimethyl-3-nitrophenyl)methyl cis- and trans-3-(2-chloro-3,3,3-trifluoropropenyl)-2,2-dimethylcyclopropanecarboxylate were prepared by reacting (2,6-dimethyl-3-nitrophenyl)methanol with either cis- or trans-3-(2-chloro-3,3,3-trifluoropropenyl)-2,2-dimethylcyclopropanecarboxylic acid chloride, respectively.

Analysis of (2,6-dimethyl-3-nitrophenyl)methyl cis-3-(2-chloro-3,3,3-trifluoropropenyl)-2,2-dimethylcyclopropanecarboxylate:
Calc'd for $C_{18}H_{19}ClF_3NO_4$: C, 53.27; H, 4.72; O, 3.45; Found: C, 52.96; H, 4.63; O, 3.28.
nmr: 1.26 (s,6H); 1.48–2.16 (m,2H); 2.41 (s,3H); 2.45 (s,3H); 5.19 (s,2H); 6.72–7.69 (m,3H).

Analysis of (2,6-dimethyl-3-nitrophenyl)methyl trans-3-(2-chloro-3,3,3-trifluoropropenyl)-2,2-dimethylcyclopropanecarboxylate:
Calc'd for $C_{18}H_{19}ClF_3NO_4$: C, 53.27; H, 4.72; O, 3.45; Found: C, 53.43; H, 4.86; O, 3.34.
nmr: 1.23 (s,3H); 1.33 (s,3H); 1.53–1.80 (m,2H); 2.50 (s,3H); 2.51 (s,3H); 5.33 (s,2H); 6.09–6.26 (d,1H); 7.83–8.49 (m,2H).

In the same way, (2,6-dimethyl-3-nitrophenyl)methyl 3-(2-bromo-3,3,3-trifluoropropenyl)- and 3-(2,3,3,3-tetrafluoropropenyl)-2,2-dimethylcyclopropanecarboxylate are prepared by reacting the corresponding acid chlorides with (2,6-dimethyl-3-nitrophenyl)methanol.

In the same way, (2,6-dimethyl-3-nitrophenyl)methyl 2,2,3,3-tetramethylcyclopropanecarboxylate was prepared by reacting (2,6-dimethyl-3-nitrophenyl)methanol with 2,2,3,3-tetramethylcyclopropanecarboxylic acid chloride.

Analysis:
Calc'd for $C_{17}H_{23}NO_4$: C, 66.86; H, 7.59; Found: C, 67.10; H, 7.39.

nmr: 1.17 (s,6H); 1.23 (s,6H); 2.43 (s,3H); 2.46 (s,3H); 5.19 (s,2H); 7.08–7.73 (m,2H).

(3-Amino-2,6-dimethylphenyl)methyl esters corresponding to the above are prepared by techniques known in the art, including substituting (3-amino-2,6-dimethylphenyl)methanol for (2,6-dimethyl-3-nitrophenyl)methanol and protecting the amino group.

EXAMPLE 2

Preparation of (3-Amino-2,6-dimethylphenyl)methyl Esters (2,6-Dimethyl-3-nitrophenyl)methyl cis-3-(2-chloro-3,3,3-trifluoropropenyl)-2,2-dimethylcyclopropanecarboxylate (11.27 grams, 0.028 mole) was hydrogenated over Raney nickel. The product was chromatographed on an alumina column eluted with toluene to give (3-amino-2,6-dimethylphenyl)methyl cis-3-(2-chloro-3,3,3-trifluoropropenyl)2,2-dimethylcyclopropanecarboxylate (3.45 grams) as a liquid.

Analysis:
Calc'd for $C_{18}H_{21}ClF_3NO_2$: C, 57.52; H, 5.63; Found: C, 58.33; H, 5.53.

nmr: 1.26 (s,3H); 1.30 (s,3H); 1.88–2.01 (m,2H); 2.15 (s,3H); 2.28 (s,3H); 4.00 (s,2H); 5.21 (s,2H); 6.54–7.01 (m,3H).

In a similar manner, (3-amino-2,6-dimethylphenyl)methyl cis,trans-3-(2,2-dichloroethenyl)-2,2-dimethylcyclopropanecarboxylate (cis:trans 42:58) was prepared by substituting (2,6-dimethyl-3-nitrophenyl)methyl 3-(2,2-dichloroethenyl)-2,2-dimethylcyclopropanecarboxylate for (2,6-dimethyl-3-nitrophenyl)-methyl cis-3-(2-chloro-3,3,3-trifluoropropenyl)-2,2-dimethylcyclopropanecarboxylate.

Analysis:
Calc'd for $C_{17}H_{21}Cl_2NO_2$: C, 59.65; H, 6.19; O, 4.09; Found: C, 60.25; H, 6.25; O, 4.46.

nmr: 1.13–1.26 (m,12H); 1.53–2.00 (m,4H); 2.16 (s,6H); 2.30 (s,6H); 3.51 (s,4H); 5.21 (s,4H); 5.52–5.66 (d,1H); 6.23–6.33 (s,1H); 6.53–6.96 (m,4H).

Similarly, the other (3-amino-2,6-dimethylphenyl)methyl esters of this invention are prepared by reducing the corresponding (2,6-dimethyl-3-nitrophenyl)methyl esters.

EXAMPLE 3

Preparation of (3-Isothiocyanoato-2,6-dimethylphenyl)methyl Esters

Triethylamine (0.5 gram, 0.005 mole) was added to a solution of (3-amino-2,6-dimethylphenyl)methyl cis-3-(2-chloro-3,3,3-trifluoropropenyl)-2,2-dimethylcyclopropanecarboxylate (2.03 grams, 0.005 mole) in chloroform (20 ml) and cooled to 0°. Thiophosgene (0.58 gram, 0.005 mole) was added, and the reaction mixture was allowed to come to room temperature. The solvent was evaporated, and the residue was dissolved in diethyl ether. The solution was washed with water, dried over magnesium sulfate and filtered. The solvent was evaporated to give (3-isothiocyanato-2,6-dimethylphenyl)methyl cis-3-(2-chloro-3,3,3-trifluoropropenyl)-2,2-dimethylcyclopropanecarboxylate (1.71 grams, mp 60°).

Analysis:
Calc'd for $C_{19}H_{19}ClF_3NO_2S$: C 54.61; H 4.58; Found: C 54.20; H 4.30.

Similarly, the trans and the cis,trans esters are prepared from the trans and the cis,trans esters.

(3-Isothiocyanato-2,6-dimethylphenyl)methyl 3-(2,2-dihaloethenyl)-2,2-dimethylcyclopropanecarboxylates are prepared as described above, and by the same procedure, (3-isothiocyanate-2,6-dimethylphenyl)methyl 2,2,3,3-tetramethylcyclopropanecarboxylate is prepared via the corresponding (3-amino-2,6-dimethylphenyl)methyl ester.

EXAMPLE 4

Preparation of (3-Bromo-2,6-dimethylphenyl)methyl Esters

3-Bromo-2,6-dimethylbenzoic acid was prepared from 2,6-dimethylbenzoic acid by treatment with bromine in acetic acid; see Org. Synth. Coll., Vol. 3, 138 (1944). 3-Bromo-2,6-dimethylbenzoic acid was esterified with methyl iodide as described in Tet. Letters, 689 (1973) to give methyl 3-bromo-2,6-dimethylbenzoate.

Using dried glassware, a solution of lithium aluminum hydride (0.79 gram, 0.021 mole) in dry tetrahydrofuran (90 ml) was cooled in a dry ice/acetone bath (78° C.) under a nitrogen atmosphere, and methyl 3-bromo-2,6-dimethylbenzoate (5.0 grams, 0.021 mole) in dry tetrahydrofuran (10 ml) was added. The mixture was stirred at room temperature for four hours, and a mixture of tetrahydrofuran (9 ml) in water (1 ml) was added, followed by water (10 ml) and 3 N hydrochloric acid until the solution was acidic. The reaction mixture was extracted with three 200 ml portions of diethyl ether. The combined extracts were dried over magnesium sulfate, filtered and the solvent evaporated to give (3-bromo-2,6-dimethylphenyl)methanol (5.8 grams). The ir spectrum was consistent with the named compound.

(3-Iodo-, (3-fluoro-, and (3-chloro-2,6-dimethylphenyl)-methanol are prepared from the corresponding 3-iodo-, 3-fluoro-, and 3-chloro-2,6-dimethylbenzoic acids by the same method.

Using dried glassware, pyridine (2.13 grams, 0.027 mole) was added to a stirred solution of (3-bromo-2,6-dimethylphenyl)methanol (5.8 grams, 0.027 mole) in dry toluene (90 ml), and the mixture was cooled to 0°. A solution of 3-(2,2-dichloroethenyl)-2,2-dimethylcyclopropane acid chloride (5.9 grams, 0.026 mole, cis:trans 40:60) in dry toluene (10 ml) was added dropwise, and the reaction mixture was stirred in an ice bath for 16 hours. The mixture was poured over crushed ice (200 ml) and extracted with three 50 ml portions of chloroform. The combined extracts were washed successively with 50 ml portions of cold aqueous 5% hydrochloric acid, water, saturated aqueous sodium bicarbonate solution, and water. The washed extracts were dried over magnesium sulfate, filtered and the solvent evaporated. The residue was distilled and then chromatographed on a silica gel column. The product was distilled again and chromatographed on a silica gel column, elution with hexane and hexane/methylene chloride mixtures, to give two fractions, A (0.23 gram), which eluted first, and B (0.37 gram).

Analysis of A:

Calc'd for $C_{17}H_{19}BrCl_2O_2$: C, 50.27; H, 4.72; Found: C, 50.35; H, 4.74.

nmr: 1.23 (s,3H); 1.26 (s,3H); 1.71–2.15 (m,2H); 2.33 (s,3H); 2.46 (s,3H); 5.23 (s,2H); 6.19–6.33 (d,1H); 6.86–7.54 (m,2H).

The nmr spectrum was consistent with (3-bromo-2,6-dimethylphenyl)-methyl cis-3-(2,2-dichloroethenyl)-2,2-dimethylcyclopropanecarboxylate. The 1R-cis isomer was similarly prepared from 1R-cis-3-(2,2-dichloroethenyl)-2,2-dimethylcyclopropane acid chloride.

Analysis of B:

Calc'd for $C_{17}H_{19}BrCl_2O_2$: C, 50.27; H, 4.72; Found: C, 50.39; H, 4.80.

nmr: 1.17 (s,3H); 1.30 (s,3H); 1.53–2.26 (m,2H); 2.36 (s,3H); 2.46 (s,3H); 5.23 (s,2H); 5.53–5.66 (d,1H); 7.13–7.81 (m,2H).

The nmr spectrum was consistent with (3-bromo-2,6-dimethylphenyl)methyl trans-3-(2,2-dichloroethenyl)-2,2-dimethylcyclopropanecarboxylate.

In a similar manner, reacting (3-bromo-2,6-dimethylphenyl)methanol with cis- and trans-3-(2-chloro-3,3,3-trifluoropropenyl)-2,2-dimethylcyclopropanecarboxylic acid chloride, (3-bromo-2,6-dimethylphenyl)methyl cis- and trans-3-(2-chloro-3,3,3-trifluoropropenyl)-2,2-dimethylcyclopropanecarboxylate were prepared.

Analysis of cis isomer:

Calc'd for $C_{18}H_{19}BrClF_3O_2$: C, 45.25; H, 4.00; Found: C, 49.65; H, 4.33.

nmr: 1.30 (s,6H); 1.90–2.20 (m,2H); 2.35 (s,3H); 2.46 (s,3H), 5.26 (s,2H); 6.89–7.58 (m,3H).

Analysis of trans isomer:

nmr: 1.17 (s,3H), 1.26 (s,3H); 1.50–1.76 (m,2H); 2.30 (s,3H); 2.50 (s,3H); 5.29 (s,2H); 6.08–6.24 (d,1H); 6.89–7.56 (m,2H).

In a similar manner, reacting (3-bromo-2,6-dimethylphenyl)methanol with 2,2,3,3-tetramethylcyclopropanecarboxylic acid chloride, (3-bromo-2,6-dimethylphenyl)methyl 2,2,3,3-tetramethylcyclopropanecarboxylate is prepared. Similarly, reacting (3-bromo-2,6-dimethylphenyl)methanol with other 3-(2,2-dihaloethenyl)-2,2-dimethylcyclopropanecarboxylic acid chlorides or 3-(2-halo-3,3,3-trifluoropropenyl)-2,2-dimethylcyclopropane carboxylic acid chlorides yields the corresponding (3-bromo-2,6-dimethylphenyl)methyl esters.

When the aforesaid acid chlorides react with (3-iodo-, (3-fluoro, or (3-chloro-2,6-dimethylphenyl)methanol, on the other hand, the corresponding (3-iodo-2,6-dimethylphenyl)methyl, (3-fluoro-2,6-dimethylphenyl)methyl, and (3-chloro-2,6-dimethylphenyl)methyl esters result.

EXAMPLE 5

Preparation of (3-Cyano-2,6-dimethylphenyl)methyl Esters

3-Bromo-2,6-dimethylbenzoate was treated with cuprous cyanide according to the method of J. Org. Chem., 26, 2525 (1961) to afford methyl 3-cyano-2,6-dimethylbenzoate. Methyl 3-cyano-2,6-dimethylbenzoate was hydrolyzed to give 3-cyano-2,6-dimethylbenzoic acid.

A solution of 3-cyano-2,6-dimethylbenzoic acid (8.11 grams, 0.049 mole) in tetrahydrofuran (100 ml) was cooled to 0°. Borane (48.7 grams, 0.049 mole) in tetrahydrofuran was added dropwise over a 20 minute period. The mixture was allowed to come to room temperature, and water was added. Potassium carbonate was added to separate the layers. The aqueous layer was extracted with diethyl ether. The extract was added to the organic phase, which was dried over magnesium sulfate, filtered, and the solvent evaporated to give (3-cyano-2,6-dimethylphenyl)methanol (2.93 grams).

Analysis:

nmr: 2.30–2.60 (m,6H); 3.38 (s,1H); 4.43–4.86 (m,2H); 6.98–7.46 (m,2H).

Cis-3-(2-chloro-3,3,3-trifluoropropenyl)-2,2-dimethylcyclopropanecarboxylic acid chloride (4.28 g, 0.018 mole) was added dropwise to a cooled solution of (3-cyano-2,6-dimethylphenyl)-methanol (2.93 grams, 0.018 mole) and pyridine (1.5 grams, 0.02 mole) in toluene (100 ml), and the mixture was allowed to come to room temperature. The solution was poured over crushed ice and extracted with methylene chloride. The combined organic extracts were washed successively with water, 5% aqueous hydrochloric acid, water, and saturated aqueous sodium bicarbonate solution. The organic phase was dried with magnesium sulfate, filtered and the solvent evaporated. The residue was chromatographed on a silica gel column, elution with heptane, then heptane/methylene chloride to give (3-cyano-2,6-dimethylphenyl)methyl cis-3-(2-chloro-3,3,3-trifluoropropenyl)-2,2-dimethylcyclopropanecarboxylate (1.11 grams, mp 98°).

Analysis:

Calc'd for $C_{19}H_{19}ClF_3NO_3$: C, 59.15; H, 4.46; Found: C, 59.05; H, 5.15.

nmr: 1.30 (s,6H); 1.50–2.16 (m,2H); 2.43 (s,3H); 2.56 (s,3H); 5.33 (s,2H); 6.81–7.56 (m,3H).

In a similar manner, (3-cyano-2,6-dimethylphenyl)methanol is reacted with other 3-(2-halo-3,3,3-trifluoropropenyl)-2,2-dimethylcyclopropanecarboxylic acid chlorides and others 3-(2,2-dihaloethenyl)-2,2-dimethylcyclopropanecarboxylic acid chlorides, or 2,2,3,3-tetramethylcyclopropanecarboxylic acid chloride to give other (3-cyano-2,6-dimethylphenyl)methyl 3-(2-halo-3,3,3-trifluoropropenyl)-2,2-dimethylcyclopropanecarboxylates and 3-(2,2-dihaloethenyl)-2,2-dimethylcyclopropanecarboxylates within the scope of this invention, or (3-cyano-2,6-dimethylphenyl)methyl 2,2,3,3-tetramethylcyclopropanecarboxylate, respectively.

EXAMPLE 6

Preparation of (3-Iodo-2,6-dimethylphenyl)methyl Esters

A solution of sodium nitrite (12.7 g) in water (15 ml) was added dropwise to a stirred mixture of (3-amino-2,6-dimethylphenyl)methyl cis-3-(2-chloro-3,3,3-trifluoropropenyl)-2,2-dimethylcyclopropanecarboxylate (9.5 g, 0.025 mole) and concentrated sulfuric acid (20.9 g) in water (120 ml), while maintaining the temperature at 0°. The mixture was stirred at 0° for an additional 0.5 hour, and concentrated sulfuric acid (5 ml) was added. A solution of potassium iodide (34.8 g) in water (25 ml) was added dropwise, followed by copper powder (0.2 g). The reaction mixture was slowly heated to 70°. After heating at 70° for one hour the reaction mixture was allowed to cool and was stirred for 16 hours. The reaction mixture was then extracted with three 300 ml portions of methylene chloride. The combined extracts were washed twice with 500 ml of saturated aqueous sodium bisulfite solution and once with 500 ml of saturated aqueous sodium chloride solution, dried over magnesium sulfate, filtered, and the solvent evaporated to give (3-iodo-2,6-dimethylphenyl)methyl cis-3-(2- chloro-3,3,3-trifluoropropenyl)-2,2-dimethylcyclopropanecarboxylate (9.89 g).

Analysis:

Calc'd for $C_{18}H_{19}ClF_3IO_2$: C, 44.41; H, 3.93; Found: C, 45.54; H, 4.78.

The nmr spectrum was consistent with the named compound. The cis,trans- and trans-isomers are similarly prepared from the appropriate (3-amino-2,6-dimethylphenyl)methyl 3-(2-chloro-3,3,3-trifluoropropenyl)-2,2-dimethylcyclopropanecarboxylates.

Other (3-iodo-2,6-dimethylphenyl)methyl 3-(2-halo-3,3,3-trifluoropropenyl)-2,2-dimethylcyclopropanecarboxylates of this invention, (3-iodo-2,6-dimethylphenyl)methyl 3-(2,2-dihaloethenyl)-2,2-dimethylcyclopropanecarboxylates and (3-iodo-2,6-dimethylphenyl)methyl 2,2,3,3-tetramethylcyclopropanecarboxylate are prepared similarly from the corresponding (3-amino-2,6-dimethylphenyl)methyl cyclopropanecarboxylates.

The 3-chloro and 3-fluoro compounds corresponding to the above-identified iodo esters are prepared as follows. To prepare the corresponding chloro compounds, cuprous chloride is substituted for the potassium iodide and copper employed in the above-described procedure. On the other hand, if the combination of potassium iodide and copper is replaced by fluoroboric acid, the corresponding (3-fluoro-2,6-dimethylphenyl)methyl esters result.

EXAMPLE 7

Preparation of (2,6-Dimethyl-3-lower alkyl phenyl)methyl Esters

Morpholine (13.34 g), isovaleraldehyde (13.18 g), p-toluenesulfonic acid (0.2 g), and toluene (300 ml) were combined and heated at reflux using a Soxhlet extractor with magnesium sulfate to remove any water produced. After three hours the Soxhlet extractor was replaced with a condenser, and ethyl 4,6-dimethyl-2-oxo-2H-pyran-5-carboxylate (30 g) was added. The reaction mixture was heated under reflux for approximately 64 hours. The solvent was evaporated, and the resultant oil was distilled to give 11.1 g of crude product which was chromatographed to yield ethyl 2,6-dimethyl-3-(1-methylethyl)benzoate (2.8 g).

A solution of ethyl 2,6-dimethyl-3-(1-methylethyl)benzoate (2.8 g) in dry 1,2-dimethoxyethane (40 ml) was added dropwise under a nitrogen atmosphere to a stirred solution of lithium aluminum hydride in dry 1,2-dimethoxyethane (80 ml) at approximately $-78°$. The mixture was allowed to warm to ambient temperature. The mixture was heated to reflux and maintained under reflux for one hour. After cooling to ambient temperature, a solution of 1,2-dimethoxyethane (20 ml) in water (5 ml) was added dropwise to the reaction mixture, followed by additional water (25 ml). The reaction mixture was acidified with 3 N hydrochloric acid and extracted with diethyl ether. The combined ether extracts were dried over magnesium sulfate, filtered, and the solvent evaporated to give [2,6-dimethyl-3-(1-methylethyl)phenyl]methanol (1.7 g). The nmr spectrum was consistent with the proposed structure.

[2,6-Dimethyl-3-(1-methylethyl)phenyl]methanol (0.7 g, 0.004 mole), cis-3-(2-chloro-3,3,3-trifluoropropenyl)-2,2-dimethylcyclopropanecarboxylic acid chloride (0.97 g, 0.004 mole), pyridine (2 ml) and dry toluene (150 ml) were combined to give [2,6-dimethyl-3-(1-methylethyl)phenyl]methyl cis-3-(2-chloro-3,3,3-trifluoropropenyl)-2,2-dimethylcyclopropanecarboxylate.

Analysis:

Calc'd for $C_{21}H_{26}ClF_3O_2$: C, 62.60; H, 6.50; Found: C, 62.05; H, 5.98.

nmr: 1.15–1.30 (m,12H); 1.46–2.16 (m,3H); 2.33 (s,6H); 5.23 (s,2H); 6.83–7.23 (m,3H).

Other isomers, such as the cis,trans- and trans-esters are similarly prepared by reacting the appropriate acid chloride.

In a similar manner, other [2,6-dimethyl-3-(1-methylethyl)phenyl] methyl 3-(2-halo-3,3,3-trifluoropropenyl)-2,2-dimethylcyclopropanecarboxylates, 3-(2,2-dihaloethenyl)-2,2-dimethylcyclopropanecarboxylates and [2,6-dimethyl-3-(2-methylethyl)phenyl]methyl 2,2,3,3-tetramethylcyclopropanecarboxylate are prepared by reacting [2,6-dimethyl-3-(1-methylethyl)phenyl]methanol with the appropriate acid chlorides.

Other esters, those wherein the 3-substituent in the alcohol is lower alkyl other than 1-methylethyl, e.g., methyl, ethyl, n-propyl, butyl, pentyl, hexyl, iso-butyl, sec-butyl, etc. are similarly prepared by reacting the appropriate acid chloride with an appropriate (2,6-dimethyl-3-lower alkyl phenyl)methanol. These alcohols, in turn, are prepared by the method described above, substituting an aldehyde of appropriate structure for the isovaleraldehyde. For example, propanal gives rise to (2,3,6-trimethylphenyl)methanol, butyraldehyde to (2,6-dimethyl-3-ethylphenyl)methanol, 4-methylpentanal to (2,6-dimethyl-3-isobutylphenyl)methanol, 3-methylpentanal to (2,6-dimethyl-3-sec-butylphenyl)methanol, etc.

In the normal use of the insecticidal and acaricidal esters of the present invention, the esters usually will not be employed free from admixture or dilution, but ordinarily will be used in a suitable formulated composition compatible with the method of application and comprising an insecticidally or acaricidally effective amount of (2,6-dimethyl-3-substituted phenyl)methyl cyclopropanecarboxylate. The esters of this invention, like most pesticidal agents, may be blended with the agriculturally acceptable surface-active agents and carriers normally employed for facilitating the dispersion of active ingredients, recognizing the accepted fact that the formulation and mode of application of an insecticide or acaricide may affect the activity of the material. The present esters may be applied, for example, as sprays, dusts, or granules to the area where pest control is desired, the type of application varying of course with the pest and the environment. Thus, the esters of this invention may be formulated as granules of large particle size, as powdery dusts, as wettable powders, as emulsifiable concentrates, as solutions, and the like.

Granules may comprise porous or nonporous particles, such as attapulgite clay or sand, for example, which serve as carriers for the esters. The granule particles are relatively large, a diameter of about 400–2500 microns typically. The particles are either impregnated with the ester from solution or coated with the ester, adhesive sometimes being employed. Granules generally contain 1–15%, preferably 3–10%, active ingredient as the insecticidally effective amount.

Dusts are admixtures of the esters with finely divided solids such as talc, attapulgite clay, kieselguhr, pyrophyllite, chalk, diatomaceous earths, calcium phosphates, calcium and magnesium carbonates, sulfur, flours, and other organic and inorganic solids which act as carriers for the insecticide. These finely divided solids have an average particle size of less than about 50 microns. A typical dust formulation useful for controlling insects and acarids contains 10 parts of (2,6-dimethyl-3-substituted phenyl)methyl cyclopropanecarboxylate, such as (2,6-dimethyl-3-nitrophenyl)methyl 3-(2-chloro-3,3,3-trifluoropropenyl)-2,2-dimethylcyclopropanecarboxylate, 30 parts of bentonite clay, and 60 parts of talc.

The esters of the present invention may be made into liquid concentrates by dissolution or emulsification in suitable liquids and into solid concentrates by admixture with talc, clays, and other known solid carriers used in the pesticide art. The concentrates are compositions containing, as an insecticidally or acaricidally effective amount, about 5–50% (2,6-dimethyl-3-substituted phenyl)methyl cyclopropanecarboxylate, such as (2,6-dimethyl-3-nitrophenyl)methyl 3-(2-chloro-3,3,3-trifluoropropenyl)-2,2-dimethylcyclopropanecarboxylate, and 95–50% inert material, which includes surface-active dispersing, emulsifying, and wetting agents. The concentrates are diluted with water or other liquids for practical application as sprays, or with additional solid carrier for use as dusts.

Typical carriers for solid concentrates (also called wettable powders) include fuller's earth, clays, silicas, and other highly absorbent, readily wetted inorganic diluents. A solid concentrate formulation useful for controlling insects and acarids contains 1.5 parts each of sodium lignosulfonate and sodium laurylsulfate as wetting agents, 25 parts of (3-bromo-2,6-dimethylphenyl)methyl 3-(2,2-dichloroethenyl)-2,2-dimethylcyclopropanecarboxylate, and 72 parts of bentonite clay.

Useful liquid concentrates include the emulsifiable concentrates, which are homogeneous liquid or paste compositions readily dispersed in water or other liquid carriers. They may consist entirely of the ester with a liquid or solid emulsifying agent, or they may also contain a liquid carrier such as xylene, heavy aromatic naphthas, isophorone and other relatively nonvolatile organic solvents. For application, these concentrates are dispersed in water or other liquid carriers and normally applied as sprays to areas to be treated.

Typical surface-active wetting, dispersing, and emulfifying agents used in pesticidal formulations include, for example, the alkyl and alkylaryl sulfonates and sulfates and their sodium salts; alkylamide sulfonates, including fatty methyl taurides; alkylaryl polyether alcohols, sulfated higher alcohols, polyvinyl alcohols; polyethylene oxides; sulfonated animal and vegetable oils; sulfonated petroleum oils; fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises about 1–15% by weight of the insecticidal and acaricidal composition.

Other useful formulations include simple solutions of the active ingredient in a solvent in which it is completely soluble at the desired concentration, such as acetone or other organic solvents.

As insecticidally or acaricidally effective amount of (2,6-dimethyl-3-substituted phenyl)methyl cyclopropanecarboxylate in an insecticidal or acaricidal composition diluted for application is normally in the range of about 0.001% to about 2% by weight. Many variations of spraying and dusting compositions known in the art may be used by substituting the esters of this invention into compositions known or apparent to the art.

The insecticidal or acaricidal compositions of this invention may be formulated with other active ingredients, including other insecticides, nematicides, acaricides, fungicides, plant growth regulators, fertilizers, etc. In using the compositions to control insects and acarids, it is only necessary that an insecticidally or acaricidally effective amount of (2,6-dimethyl-3-substituted phenyl)methyl cyclopropanecarboxylate be applied to the locus where control is desired. For most applications, an insecticidally or acaricidally effective amount will be about 75 to 4000 g per hectare, preferably 150 g to 3000 g per hectare.

The insecticidal and acaricidal activity of the (2,6-dimethyl-3-substituted phenyl)methyl cyclopropanecarboxylates whose preparation is described above were evaluated as follows:

The activity was evaluated in topical application to southern armyworm (*Spodoptera eridania*), Mexican bean beetle (*Epilachna varivestis*), large milkweed bug (*Oncopeltus fasciatus*), cabbage looper (*Trichoplusia ni*), and tobacco budworm (*Heliothis virescens*). Two replicates of 10 test larvae per replicate were placed in 9 cm petri dishes, each lined with a piece of filter paper and a food source. On the second or third dorsal thoracic segment of each larva was placed a 1 microliter droplet containing the desired amount of the test compound in acetone. The toxic effect of the compound was determined 24 hours after application. An insect was considered dead if it could no longer right itself and move in an oriented pattern. The results of these tests appear in Table I.

The compounds were also tested in foliar applications at various concentrations in aqueous solutions containing 10% acetone and 0.25% emulsifier. The plants (English fava bean for pea aphid and pinto bean for the remaining species) were placed on a revolving turntable in a hood, and the test solutions were applied with a sprayer. The test solutions were applied to the upper and lower surfaces of the plant leaves while the turntable revolved 10 times (5 for upper surface and 5 for lower surface). The total spray time was approximately one minute, and the leaves were covered to runoff. In every case the lowest rate was applied first and the highest rate last. The plants were then allowed to dry. The treated leaves were removed and placed in 240 ml or 480 ml wax treated containers. Ten individuals of the appropriate species were placed in each container and the container capped. Mortality was read 48 hours post-treatment unless otherwise noted. Two replicates of ten individuals were made at each rate. Foliar evaluation used southern armyworm (*Spodoptera eridania*), Mexican bean beetle (*Epilachna varivestis*), pea aphid (*Acyrthosiphon pisum*), and twospotted spider mite (*Tetranychus urticae*). The results of the foliar tests appear in Table II.

TABLE I

| Compound | | Topical Evaluation Insects[a] | | | | |
|---|---|---|---|---|---|---|
| Acid Moiety[c] | 3-substituent | SAW $LD_{50}$[b] | MBB $LD_{50}$[b] | CL $LD_{50}$[b] | MWB $LD_{50}$[b] | TBW $LD_{50}$[b] |
| cis-TFP | —NO$_2$ | 77–88 | 13–14 | 530 | 1300–1400 | 2200 |
| trans-TFP | —NO$_2$ | 83 | 36 | 340 | 12000 | 200 |
| cis-DCE | —NO$_2$ | 92 | 51 | 62 | 1200 | |
| (1R)-cis-DCE | —NO$_2$ | 92 | 61 | 490 | 920 | 140 |

TABLE I-continued

Topical Evaluation

| Compound | | Insects[a] | | | | |
|---|---|---|---|---|---|---|
| Acid Moiety[c] | 3-substituent | SAW LD$_{50}$[b] | MBB LD$_{50}$[b] | CL LD$_{50}$[b] | MWB LD$_{50}$[b] | TBW LD$_{50}$[b] |
| cis,trans-DCE | —NO$_2$ | 130 | | | | |
| TM | —NO$_2$ | 710 | 120 | | 1600 | |
| cis,trans-DCE | —NH$_2$ | | 2700 | | | |
| cis-TFP | —Br | 300 | 160 | | 3800 | |
| trans-TFP | —Br | 480 | 320 | | | |
| cis-DCE | —Br | 99 180 | | 880 | | |
| (1R)-cis-DCE | —Br | 270 | 1100 | | 2500 | |
| trans-DCE | —Br | 140 | | 720 | | |
| cis-TFP | —CN | 290 | 18 | | 2700 | |
| cis-TFP | —NCS | 310 | 63–94 | | | |
| cis-DCE | —isopropyl | 66 | 52 | 210 | 430 | 140 |
| cis-TFP | —isopropyl | 76 | 20 | 190 | 560 | 110 |
| cis-TFP | —I | 160 | 37 | 310 | 940 | 110 |

[a]SAW = Southern armyworm
MBB = Mexican bean beetle
CL = Cabbage looper
MWB = Milkweed bug
TBW = Tobacco budworm
[b]ng/insect
[c]TFP = 3-(2-chloro-3,3,3-trifluoropropenyl)-2,2-dimethylcyclopropyl
DCE = 3-(2,2-dichloroethenyl)-2,2-dimethylcyclopropyl
TM = 2,2,3,3-tetramethylcyclopropyl

TABLE II

Foliar Evaluation

| Compound | | Concentration | Mortality (% killed)[a] | | | |
|---|---|---|---|---|---|---|
| Acid Moiety[b] | 3-substituent | (ppm) | SAW | MBB | PA | TSM |
| cis-TFP | —NO$_2$ | 64 | 100 | 100 | 100 | 21 |
| | | 3.2 | | 100 | | |
| trans-TFP | —NO$_2$ | 16 | 55 | 30 | 5 | |
| cis-DCE | —NO$_2$ | 312 | | | | 100 |
| | | 5 | 88 | 100 | 18 | |
| (1R)-cis-DCE | —NO$_2$ | 32 | 100 | 100 | 65 | |
| cis,trans-DCE | —NO$_2$ | 312 | | | | 36 |
| | | 78 | 100 | 100 | 76 | |
| TM | —NO$_2$ | 500 | | | 15 | |
| | | 48 | | 100 | | |
| cis-TFP | —NH$_2$ | 500 | | | 100 | |
| cis,trans-DCE | —NH$_2$ | 500 | | | 74 | |
| cis-TFP | —Br | 16 | 65 | 100 | 10 | |
| trans-TFP | —Br | 32 | 80 | 50 | 15 | |
| (1R)-cis-DCE | —Br | 32 | | 100 | | |
| cis-TFP | —CN | 16 | 67 | 100 | 45 | |
| cis-TFP | —NCS | 64 | 100 | 95 | 95 | 87 |
| cis-DCE | —isopropyl | 500 | 100 | | 100 | 95 |
| | | 16 | 90 | 100 | 75 | |
| cis-TFP | —isopropyl | 500 | 100 | | 100 | 100 |
| | | 16 | 80 | 100 | 95 | |
| cis-TFP | —I | 500 | 100 | | 100 | 100 |
| | | 64 | 65 | 100 | 75 | |

[a]SAW = Southern armyworm
MBB = Mexican bean beetle
PA = Pea aphid
TSM = Twospotted spider mite
[b]TFP = 3-(2-chloro-3,3,3-trifluoropropenyl)-2,2-dimethylcyclopropyl
DCE = 3-(2,2-dichloroethenyl)-2,2-dimethylcyclopropyl
TM = 2,2,3,3-tetramethylcyclopropyl

What is claimed is:

1. Insecticidal and acaricidal (2,6-dimethyl-3-substituted phenyl)methyl cyclopropanecarboxylates of the formula

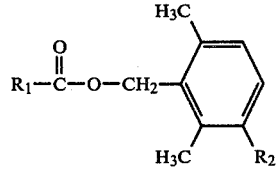

wherein R$_1$ is selected from 3-(2,2-dihaloethenyl)-2,2-dimethylcyclopropyl, 3-(2-halo-3,3,3-trifluoropropenyl)-2,2-dimethylcyclopropyl, and 2,2,3,3-tetramethylcyclopropyl and R$_2$ is selected from nitro, isothiocyanato, and amino.

2. A compound of claim 1 wherein R$_1$ is 3-(2,2-dihaloethenyl)-2,2-dimethylcyclopropyl.

3. A compound of claim 1 wherein R$_1$ is 3-(2,2-dichloroethenyl)-2,2-dimethylcyclopropyl.

4. A compound of claim 1 wherein R$_1$ is 3-(2-halo-3,3,3-trifluoropropenyl)-2,2-dimethylcyclopropyl.

5. A compound of claim 4 wherein R$_1$ is 3-(2-chloro-3,3,3-trifluoropropenyl)-2,2-dimethylcyclopropyl.

6. A compound of claim 1, 2, 3, 4, or 5 wherein R$_2$ is nitro.

7. (2,6-Dimethyl-3-nitrophenyl)methyl 3-(2-chloro-3,3,3-trifluoropropenyl)-2,2-dimethylcyclopropanecarboxylate.

8. (2,6-Dimethyl-3-nitrophenyl)methyl 3-(2,2-dichloroethenyl)-2,2-dimethylcyclopropanecarboxylate.

9. An insecticidal or acaricidal composition comprising an insecticidally or acaricidally effective amount of at least one compound of claim 1 in admixture with an agriculturally acceptable carrier.

10. A method of controlling insects or acarids which comprises applying to the locus where control is desired an insecticidally or acaricidally effective amount of at least one compound of claim 1.

* * * * *